United States Patent [19]

Yoshida et al.

[11] Patent Number: 4,572,164
[45] Date of Patent: Feb. 25, 1986

[54] LIGHT SOURCE DEVICE FOR ENDOSCOPE

[75] Inventors: Morihiko Yoshida, Omiya, Japan; David H. Cooper, Saratoga, Calif.

[73] Assignee: Fuji Photo Optical Co., Ltd., Saitama, Japan

[21] Appl. No.: 640,706

[22] Filed: Aug. 14, 1984

[30] Foreign Application Priority Data

Aug. 17, 1983 [JP] Japan .................... 58-150041

[51] Int. Cl.⁴ .............................................. A61B 1/06
[52] U.S. Cl. ........................................ 128/6; 362/373
[58] Field of Search ............... 128/4, 6; 362/294, 373

[56]  References Cited

U.S. PATENT DOCUMENTS 2,477,957  8/1949  Briskin ........................... 362/373 X
4,286,585  9/1981  Ogawa ............................. 128/6
4,419,716 12/1983  Koo ................................ 362/373 X Primary Examiner—William H. Grieb
Attorney, Agent, or Firm—Koda and Androlia

[57]  ABSTRACT

This disclosure depicts a light source device for an endoscope, incorporating a lamp to supply the light to a light guide fiber bundle for the illumination of the endoscope. This light source device for the endoscope has a heat radiating device for the light guide fiber bundle for the illumination, which has been highly heated by the radiant heat of the lamp. The radiating device includes a support ring and radiator fins radially movably mounted to and supported by the support ring via resilient members. When a light inciding end portion of the light guide fiber bundle for the illumination is installed into the light source device for the endoscope, the heat radiating device is moved radially outwardly against the biasing forces of the resilient members, and the radiator fins are reliably brought into close contact with the outer periphery of the light inciding end portion of the light guide fiber bundle. As the result, the light source device for the endoscope according to the present invention is high in radiation efficiency and can prevent the light guide fiber bundle from being highly heated.

10 Claims, 5 Drawing Figures

LIGHT SOURCE DEVICE FOR ENDOSCOPE

BACKGROUND OF THE INVENTION

1. Field of the Invention

This invention relates to a light source device for an endoscope, and more particularly to a light source device for an endoscope, incorporating a lamp for supplying the light to a light guide fiber bundle for the illumination of the endoscope.

2. Description of the Prior Art

As has been well known, the endoscope is widely used for observing the interior of a space, which is difficult to be observed from outside, in the medical and industrial fields. Most of the endoscopes are of such an arrangement that the light for the illumination necessary for the observation is obtained from the light of a lamp in an external light source device via a light guide fiber bundle for the illumination. Furthermore, in general, in the light guide fiber bundle for the illumination, a light inciding end portion (a side opposed to the lamp) is fixedly bundled by use of a bonding agent or the like and inserted into and solidly secured to a tubular protective sheath so as to be inserted into and connected to a connector on the side of the light source device. However, the light guide fiber bundle for the illumination thus arranged present such disadvantages that the bonding agent may be highly heated by radiant heat from the lamp and burned out, or, when the light guide fiber bundle for the illumination is removed from the connector, an operator may have a burn because the tubular protective sheath is considerably highly heated by the heat of the lamp.

Therefore, to obviate the above-described disadvantages, there has been proposed a light source device for an endoscope provided with heat radiating means.

For example, in the specification of Japanese Patent Publication No. 23067/65, there is disclosed heat radiating means, in which a light inciding end portion of the light guide fiber bundle for the illumination is formed into a flat shape, and this flat-shaped light inciding end portion is clamped by radiator plates from both sides to thereby radiate the heat of the light guide fiber bundle. Furthermore, in the specification of Japanese Patent Laid-Open No. 204009/82, heat radiating means, in which a heating portion of a heat pipe consisting of the heating portion, a heat transmitting portion and a heat radiating portion is brought into contact with a side surface of a light inciding end portion of the light guide fiber bundle for the illumination, to thereby lower the temperature of the light inciding end portion. Further, in the specification of Japanese Utility Model Laid-Open No. 158206/81, there is disclosed heat radiating means, in which radiator fins are provided on a socket on the side of the light source device, to which the light guide fiber bundle is connected, to thereby lower the temperature of the light guide fiber bundle.

Notwithstanding, in the heat radiating means disclosed in the aforesaid specifications, the contact between the light guide fiber bundle and the heat radiating means is unsatisfactory so that a satisfactory radiating effect cannot be obtained. More specifically, if even a small gap is formed between the light guide fiber bundle for the illumination and the heat radiating means, then no effective heat transmission is carried out from the light guide fiber bundle to the heat radiating means such as the radiator fins, so that a satisfactory heat radiating effect cannot be obtained.

SUMMARY OF THE INVENTION

The present invention has been developed to obviate the above-described disadvantages of the prior art and has as its object the provision of a light source device for an endoscope, in which reliable contact is established between the light guide fiber bundle for the illumination and the heat radiating means and the heat radiating means capable of efficiently radiating the heat is provided.

In the light source device for an endoscope according to the present invention, there are provided radiator fins radially movable with respect to the light guide fiber bundle for the illumination and these radiator fins are supported by a resilient member. When the light guide fiber bundle for the illumination is installed into the light source device for an endoscope according to the present invention, the radiator fins are brought into abutting contact with the light guide fiber bundle to move outwardly in the radial direction, to thereby be held in close contact with the light guide fiber bundle.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and therein.

DETAILED DESCRIPTION OF THE INVENTION

Description will hereunder be given of the preferred embodiments of a light source device for an endoscope according to the present invention with reference to the accompanying drawings.

Figure 1:
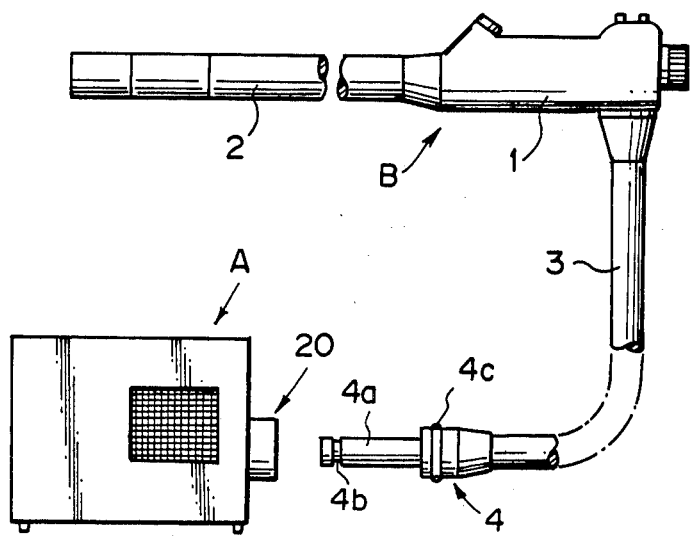
FIG. 1 is an explanatory view showing the general configurations of the endoscope and the light source device for the endoscope according to the present invention.

In FIG. 1, designated at A is a light source device for an endoscope, to which the present invention is applied and B is an endoscope which is connected to the light source device A for use. The endoscope B comprises a manual control portion 1, an insert portion 2 and a connection cable 3 to be connected to the light source device A. As shown, the connection cable 3 is connected at one end thereof to the manual control portion 1 and provided at the other end thereof with a plug portion 4 to be connected to the light source device A. The plug portion 4 is provided with a tubular protective sheath 4a formed of a high heat conductive metal, which is formed with an engageable groove 4b engageable with heat radiating fins to be described hereunder. Furthermore, a click spring ring 4c is provided on the outer periphery of the plug portion 4. A continuous light guide fiber bundle, not shown in FIG. 1, is inserted through the insert portion 2, manual control portion 1 and connection cable 3 of the endoscope B, a light inciding end face of the light guide fiber bundle is aligned with an end face of the tubular protective sheath 4a and solidly secured into the tubular protective sheath 4a, and a light exiting end face of the light guide fiber bundle is positioned at the forward end of the insert portion 2.

Figure 2:
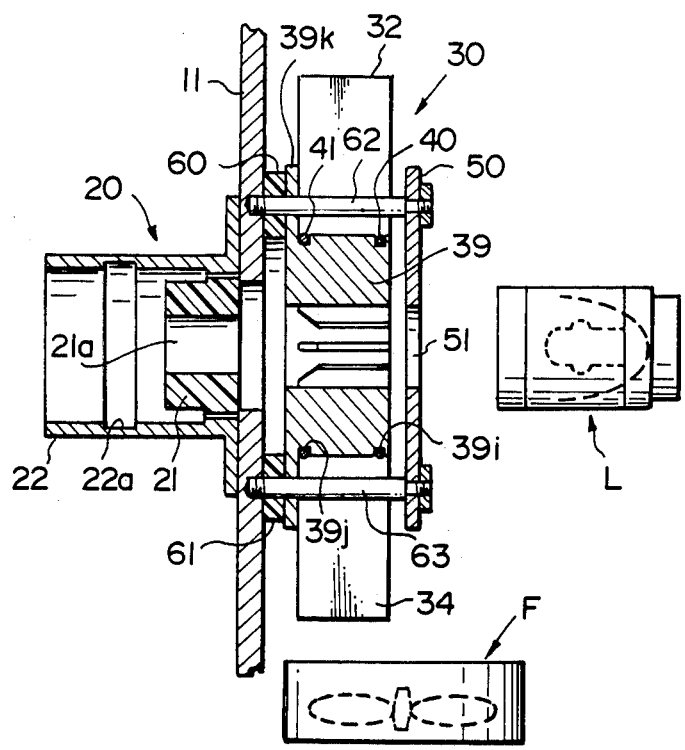
FIG. 2 is a sectional view showing the essential portions of the light source device for an endoscope according to the present invention.

FIG. 2 shows the inner construction of the light source devide A.

The light source device A assembled with the endoscope B of the above-described arrangement for use is provided on a front panel 11 directed in the illuminating direction of the light of a lamp L as being a light source as shown in FIG. 2, and has a socket portion 20 to be connected to the plug portion 4, heat radiating means 30 disposed between the socket portion 20 and the lamp L and a cooling fan F disposed downwardly of the heat radiating means 30 in FIG. 2, for cooling the heat radiating means 30. The socket portion 20 comprises a socket member 21 having a guide hole 21a for insertingly guiding the light inciding end face of the light guide fiber bundle for the illumination, integrally formed with the tubular protective sheath 4a into a predetermined light-receiving position for the lamp L, and a lock ring 22 provided on the inner peripheral portion thereof with an engageable groove 22a click-engageable with a click spring ring 4c wound around the outer periphery of the plug portion 4. Additionally, the socket member 21 is formed of an electrically insulating material for additionally functioning as a connector to electrically connect the light source device A to the endoscope B.

Figure 3:
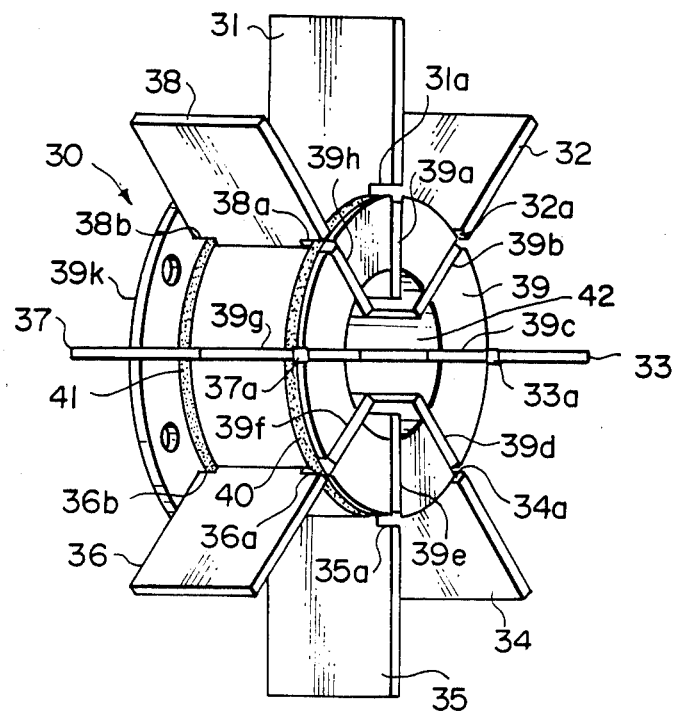
FIG. 3 is a perspective view showing the heat radiating means of the light source device for an endoscope according to the present invention.
Figure 4:
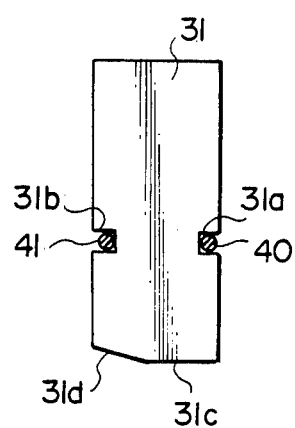
FIGS. 4 and 5 are explanatory views showing the radiator fins.
Figure 5:
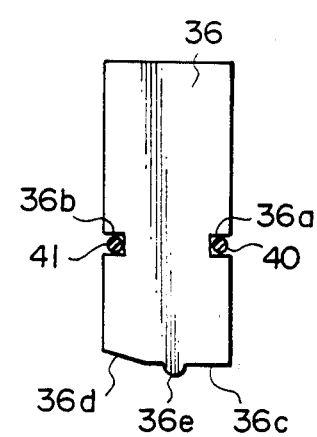

As shown in FIG. 3, the heat radiating means 30 includes a plurality of radiator fins 31 to 38 and a tubular support ring 39. The support ring 39 has a plurality of radial slits 39a to 39h for equidistantly, radially movably supporting the radiator fins 31 to 38, and further, is provided on the outer peripheries at opposite ends thereof with circular grooves 39i and 39j for receiving elastic rings 40 and 41 such as O-rings made of rubber. Further, as shown in FIG. 2, this support ring 39 is provided with a mounting flange 39k for mounting the supporting ring 39 to the inner surface of the front panel 11 in a manner to be aligned with the guide hole 21a of the socket member 21. The respective radiator fins 31 to 38 are movably inserted into the respective slits 39a and 39h of the support ring 39. At the opposite ends of the radiator fins 31 to 38, there are provided cutouts 31a to 38a and 31b to 38b, which are engageable with the elastic rings 40 and 41, respectively, as shown. Additionally, the positions of these cutouts are determined in consideration of the wall thickness and the like of the support ring 39 in such a manner that the inner diameter of a circular opening 42 formed by the inner ends 31c to 38c of the respective radiator fins 31 to 38 projecting into the support ring 39 becomes smaller than the diameter of the outer periphery of the tubular protective sheath 4a. Further, corner portions 31d to 38d of the inner ends 31c to 38c, opposed to the respective radiator fins 31 to 38 on the side of the socket portion 20 are tapered as shown in FIG. 4. At inner ends of some of the heat radiator fins, e.g. the inner end 36c of the radiator fin 36, there is provided a projection or projections engageable with the engageable groove 4c formed on the outer periphery of the tubular protective sheath 4a.

The heat radiating means 30 with the above-described arrangement together with a masking member 50 having an opening 51 are fixed to the inner surface of the front panel 11 by means of bolts 62 and 63 via insulating members 60 and 61.

In the light source device for an endoscope with the above-described arrangement, the tubular protective sheath 4a is inserted through the guide hole 21a of the socket member 21 to connect the plug portion 4 of the endoscope B to the socket portion 20, so that the light from the lamp L can be supplied to the light inciding end face of the light guide fiber bundle for the illumination.

During the aforesaid connecting operation, after the forward end of the tubular protective sheath 4a is abutted against the tapered portion 31d to 38d of the respective radiator fins 31 to 38, the forward end is further inserted, whereby the respective radiator fins 31 to 38 are moved radially outwardly against the biasing forces of the elastic rings 40 and 41, so that reliable contact between the outer peripheral surface of the tubular protective sheath 4a and the inner ends 31c to 38c of the respective radiator fins 31 to 38 can be obtained. Furthermore, a projection or projections 36e provided on some of the radiator fins 36 are engaged with the outer peripheral groove 4b of the tubular protective sheath 4a, so that the light inciding end face of the light guide fiber bundle can be accurately positioned.

In the above embodiment, two elastic rings are used, however, the present invention need not necessarily be limited to this, and, one or more than two elastic rings may be used.

In the above embodiment, the elastic rings 40 and 41 are used as the means of biasing the radiator fins 31 to 38, however, the present invention need not necessarily be limited to this, and, other publicly known resilient means such for example as coil springs and leaf springs can be used for biasing. Furthermore, the positions of engagement between the radiator fins 31 to 38 and the elastic rings 40 and 41 need not necessarily be determined by the cutouts 31a to 38a and 31b to 38b, and the outer peripheral portions of the radiator fins 31 to 38 may be abutted against the resilient members.

In the above embodiment, there is shown the example where the positioning projection 36e is provided on the radiator fin 36, however, the present invention need not necessarily be limited to this, and, all of the radiator fins may be provided thereon with positioning projections or every other radiator fins may be provided with the positioning projections.

As has been described hereinabove, the light source device for an endoscope according to the present invention can offer such advantages that, because the light guide fiber bundle for the illumination or the tubular protective sheath integrally formed thereon is brought into reliable contact with the radiator fins through the biasing forces of the resilient members, the radiating effect is high, thereby avoiding the disadvantage of the prior art, i.e. the high temperature of the light guide fiber bundle. Further, a projection or projections engageable with the light guide fiber bundle or the tubular protective sheath integrally formed thereon are provided on at least some of the radiator fins, so that the light inciding end face of the light guide fiber bundle can be accurately positioned and locked against dislodging. Furthermore, the opening formed by the respective radiator fins is variable in size, whereby the opening can accommodate itself to the light guide fiber bundles or the tubular protective sheaths integrally formed thereon, which are different from one another in diameter, so that the functional effects offered by the present invention are outstanding.

What is claimed is:

1. A light source device for an endoscope, wherein a lamp is incorporated for supplying the light to a light guide fiber bundle for the illumination of said endoscope and heat radiating means is provided which is connected to said light guide fiber bundle for the illumination when said light guide fiber bundle is inserted for connection, characterized in that said heat radiating means comprises:

a plurality of radiator fins radially movable with respect to said light guide fiber bundle for the illumination; and a resilient member or members for resiliently supporting said plurality of radiator fins and biasing the same towards said light guide fiber bundle for the illumination through the biasing forces thereof when said light guide fiber bundle for the illumination is inserted for connection.

2. A light source device for an endoscope as set forth in claim 1, wherein a light inciding end portion of said light fiber bundle for the illumination is covered by a tubular protective sheath and said radiator fins are brought into contact with said light guide fiber bundle for the illumination via said protective sheath.

3. A light source device for an endoscope as set forth in claim 1, wherein said radiator fins are movably supported by slits formed in a support ring in the radial direction thereof.

4. A light source device for an endoscope as set forth in claim 1, wherein said resilient members are elastic rings which are engaged with cutouts formed in said radiator fins to resiliently support said radiator fins.

5. A light source device for an endoscope, wherein a lamp is incorporated for supplying the light to a light guide fiber bundle for the illumination of said endoscope and heat radiating means is provided which is connected to said light guide fiber bundle for the illumination when said light guide fiber bundle is inserted for connection, characterized in that said radiating means comprises:

a support ring formed therein with a plurality of slits in the radial direction thereof;

a plurality of radiator fins supported movably in slits formed in said support ring and radially movable with respect to said light guide fiber bundle inserted for connection; and elastic rings provided on said support ring and engageable with the radiator fins, for biasing the radiator fins towards said light guide fiber bundle for the illumination through the biasing forces thereof when said light guide fiber bundle for illumination is inserted for connection.

6. A light source device for an endoscope as set forth in claim 5, wherein a light inciding end portion of said light guide fiber bundle for the illumination is covered by a tubular protective sheath and said radiator fins are brought into contact with said light guide fiber bundle for the illumination via said protective sheath.

7. A light source device for an endoscope as set forth in claim 5, wherein an inner end of each of said radiator fins on the side of the light guide fiber bundle for the illumination is tapered.

8. A light source device for an endoscope, wherein a lamp is incorporated for supplying the light to a light guide fiber bundle for the illumination of said endoscope and heat radiating means is provided which is connected to said light guide fiber bundle for the illumination when said light guide fiber bundle is inserted for connection, characterized in that said radiating means comprises:

a support ring formed therein with a plurality of slits in the radial direction thereof;

a plurality of radiator fins supported movably in slits formed in said support ring and radially movable with respect to said light guide fiber bundle inserted for connection;

a projection portion formed on an inner end of at least one of a plurality of radiator fins and engageable with an engageable groove of said light guide fiber bundle for the illumination; and elastic rings provided on said support ring and engageable with the radiator fins, for biasing the radiator fins toward said light guide fiber bundle for the illumination through the biasing forces thereof when said light guide fiber bundle for the illumination is inserted for connection.

9. A light source device for an endoscope as set forth in claim 8, wherein a light inciding end portion of said light guide fiber bundle for the illumination is covered by a tubular protective sheath and said radiator fins are brought into contact with said light guide fiber bundle for the illumination via said protective sheath.

10. A light source device for an endoscope as set forth in claim 8, wherein an inner end of each of said radiator fins on the side of the light guide fiber bundle for the illumination is tapered.

* * * * *